(12) United States Patent
Jayaraman (10) Patent No.: US 6,908,480 B2
(45) Date of Patent: Jun. 21, 2005

(54) STRUCTURALLY VARIABLE STENTS

(76) Inventor: Swaminathan Jayaraman, 459 Lowell Pl., Fremont, CA (US) 94536

( * ) Notice: Subject to any disclaimer, the term of this patent is extended or adjusted under 35 U.S.C. 154(b) by 290 days.

(21) Appl. No.: 09/941,327

(22) Filed: Aug. 29, 2001

(65) Prior Publication Data
US 2003/0045925 A1 Mar. 6, 2003

(51) Int. Cl.$^7$ .................................................. A61F 2/06
(52) U.S. Cl. ...................................... 623/1.42; 623/1.46
(58) Field of Search ................................ 606/108, 191, 606/192, 194, 195, 198; 623/1.1–1.2, 1.44–1.46; 600/3

(56) References Cited

U.S. PATENT DOCUMENTS

| | | |
|---|---|---|
| 5,650,202 A | 7/1997 | Mammone et al. |
| 5,695,714 A | 12/1997 | Kempf et al. |
| 5,700,286 A | 12/1997 | Tartaglia et al. |
| 5,722,984 A | 3/1998 | Fischell et al. |
| 5,800,511 A | 9/1998 | Mayer |
| 5,824,056 A | 10/1998 | Rosenberg |
| 5,824,077 A | 10/1998 | Mayer |
| 5,858,468 A | 1/1999 | Byrd |
| 5,871,437 A | 2/1999 | Alt |
| 5,911,754 A | 6/1999 | Kanesaka |
| 5,919,126 A | 7/1999 | Armini |
| 5,980,974 A | 11/1999 | Armini et al. |
| 6,099,561 A | 8/2000 | Alt |
| 6,146,417 A | 11/2000 | Ischinger |
| 6,161,399 A | 12/2000 | Jayaraman |
| 6,162,245 A | 12/2000 | Jayaraman |
| 6,174,329 B1 | 1/2001 | Callol et al. |
| 6,375,677 B1 * | 4/2002 | Penn et al. ................. 623/1.16 |
| 6,540,775 B1 | 4/2003 | Fischell |

* cited by examiner

Primary Examiner—Vy Bui
(74) Attorney, Agent, or Firm—Fleit Kain Gibbons Gutman Bongini & Bianco; Paul D. Bianco; Martin Fleit (57) ABSTRACT

The stent has at least two different patterns along its longitudinal length such as a closed cell and an open cell design. The stent is made from nickel/titanium, titanium, stainless steel or a noble metal. The different patterns are joined by varying articulations including a W-pattern and S-pattern. The stent has at least two coatings over the base structure, the coating depth not exceeding ten microns.

9 Claims, 8 Drawing Sheets

STRUCTURALLY VARIABLE STENTS

BACKGROUND OF THE INVENTION

This invention relates to stents used to support arterial and venous conduits in the human body. More particularly, it refers to a tubular stent having a non-uniform structure along its longitudinal length to provide good flexibility and radial strength.

There are four major classes of stents employed in the prior art. These four major classes of stents are described as follows:
1. Coil Stents are made from a single wire. The wire is bent in various ways and formed into a stent. Examples of this type of stent are those shown in U.S. Pat. Nos. 4,969,458; 4,681,110 and 5,824,056.
2. Slotted Tube Stents are laser cut using a tube of either stainless steel, nickel/titanium alloy (NITINOL®), titanium or any other suitable materials. These designs are preprogrammed into a machine language and a laser is used to cut the programs. These stents have a uniform design and a uniform thickness from the beginning to the end of the stent. In other words, the same segment is repeated from one end of the stent to the other. Examples of this type of stent are described in U.S. Pat. Nos. 4,733,665; 4,739,762; 4,776,337 and 4,793,348.
3. Self Expanding Stents are usually braided or knitted with multiple wire filaments such that they have a lower profile when stretched and they expand from a lower profile to a higher profile when unconstrained in the body. These stents are called self-expanding stents and are described in U.S. Pat. No. 4,655,771.
4. Hybrid Stents are similar to slotted tube stents except that they do not have a closed cell structure but have an open cellular structure with flexible interconnections between each segment of the design. These interconnections provide the flexibility while the segments provide the radial strength and other important properties of the stent. Examples of this stent are described in U.S. Pat. Nos. 5,514,154; 5,562,728; 5,649,952 and 5,725,572.

In use, each of the four classes of stents described above are coated as described in various patents as follows:
1. U.S. Pat. No. 5,759,174, describes a balloon that has a radiopaque segment attached to one of the longitudinal ends of the balloon. When the balloon is inflated, the stent is pressed against the ends of the artery and this indicates the center portion of the dilated stenosis. The external radiopaque marker band is typically made from a dense radiopaque metal such as tantalum, gold, platinum or an alloy of those dense metals.
2. U.S. Pat. No. 5,725,572, describes gold plating on the ends of a stent such that the gold plating marks two bands at the ends of a stent. The patentee mentions that the limitation of gold coating is the stiffening of the stent surface. Hence, the gold plating is done only at the ends where the stiffening does not significantly alter the properties of the stent. Also described is another embodiment where only the exterior of the stent is coated with a radiopaque material.
3. U.S. Pat. No. 5,919,126, describes a patent where the body of the stent is formed from a non-radioactive structural material, a radiopaque material coats the body and a beta emitting radioisotope ion is implanted into the radiopaque material.
4. U.S. Pat. No. 5,824,056 describes an implantable medical device formed from a drawn refractory metal having an improved biocompatible surface. The method by which the device is made includes coating a refractory metal article with platinum by a physical vapor deposition process and subjecting the coated article to drawing in a diamond die. The drawn article can be incorporated into an implanted medical device without removing the deposited material.
5. U.S. Pat. No. 5,824,077 describes a stent which is formed of multiple filaments arranged in two sets of oppositely directed helical windings interwoven with each other in a braided configuration. Each of the filaments is a composite including a central core and a case surrounding the core. The core is formed of a radiopaque material while the outer casing is made of a relatively resilient material, e.g., a cobalt, chromium based alloy. Alternative composite filaments described in the patent employ an intermediate barrier layer between the case and the core, a biocompatible cover layer surrounding the case, and a radiopaque case surrounding the central core.
6. U.S. Pat. No. 5,871,437 describes a non-radioactive metallic stent which is coated with a biodegradable or non-biodegradable thin coating of less than about 100 microns in thickness which is selected to avoid provoking any foreign body reaction. This coating contains a radioactive source emitting Beta particles with an activity level of approximately one micro curie and on top of this layer is an anticoagulant substance to inhibit early thrombus formation.
7. U.S. Pat. No. 6,099,561 describes a stent having a biocompatible metal hollow tube constituting a base layer having a multiplicity of openings through an open ended tubular wall thereof, the tube constituting a single member from which the entire stent is fabricated. A thin tightly adherent intermediate layer of noble metal overlies the entire exposed surface area of the tube including edges of the openings as well as exterior and interior surfaces and ends of the wall. A third outermost ceramic like layer composed of an oxide, hydroxide or nitrate of a noble metal is formed atop and in adherent relation to an intermediate layer.
8. U.S. Pat. No. 5,722,984 describes a stent which has an antithrombogenic property and contains an embedded radioisotope that makes the coating material radioactive.
9. Other relevant patents that describe the coating technology or coating properties include U.S. Pat. Nos. 5,818, 893; 5,980,974; 5,700,286; 5,858,468; 5,650,202 and U.S. Pat. No. 5,696,714.

Although some of the above mentioned stents have good flexibility and others have good radial strength, there is no optimum stent in the prior art that has both good flexibility and radial strength together with the ability to retain a useful coating.

SUMMARY OF THE INVENTION

The present invention describes a fifth class of stents having multiple designs of structurally variable configuration along the longitudinal length of the stent. The stent has one pattern at both ends of the stent to provide optimal flexibility and a different pattern at the mid-portion of the stent to provide optimal radial strength. Alternatively, the stent has one pattern at each end, a different pattern at its mid-portion and a third pattern in-between the mid-portion and each end. The stent has both closed cell and open cell configuration along its longitudinal length and the closed cells and open cells are interlinked with either straight or wavy configurations in a single stent.

A preferred pattern contains at least three different configurations selected from an open cell design, a closed cell design, a straight interlink or articulation and one wavy interlink or articulation along a variable thickness of connecting stents. Because of the variable thickness of the stents, the amount of drug loaded on the stent is varied along with the release characteristics.

The structurally variable stents of this invention usually have a stainless steel or nickel/titanium alloy (NITINOL®) base material with two layers of coating together not exceeding ten microns in depth. One layer is an undercoat in direct contact with the base metal both on the inside and outside surface of the base metal. The topmost layer is in contact with the blood. Both the undercoat and top coat are of the same material such as metallic, biological, synthetic material, or polymeric material.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION OF THE INVENTION

Throughout the following detailed description the same reference numerals refer to the same elements in all figures.

Figure 1:
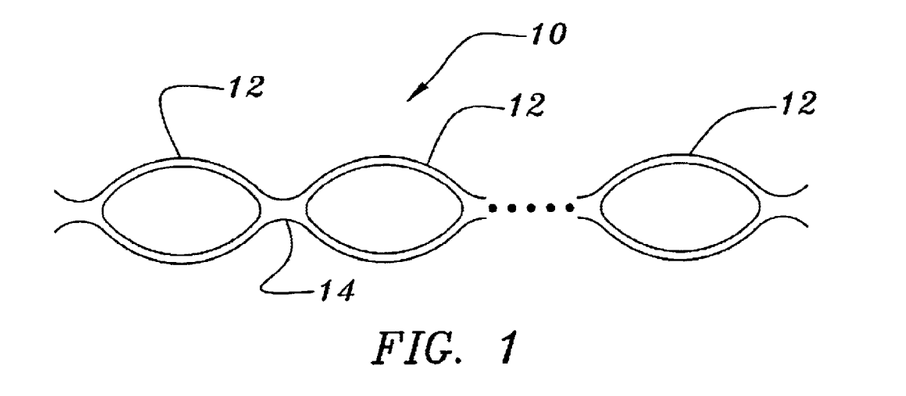
FIG. 1 shows a closed cell design of a stent.
Figure 2:
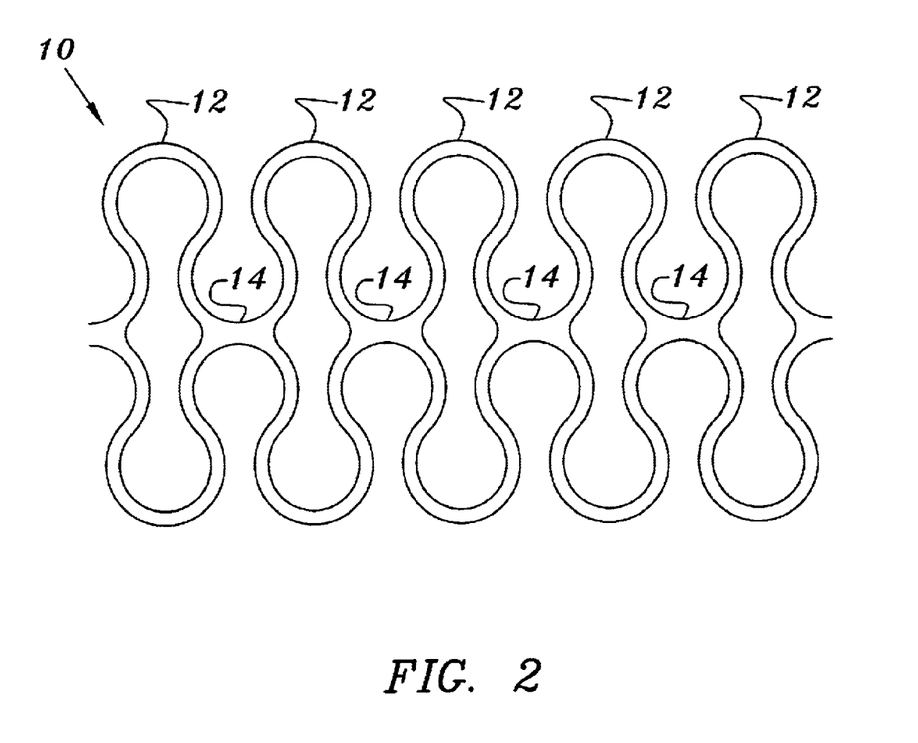
FIG. 2 shows a closed cell design of a stent interconnected by a straight bridge.
Figure 3:
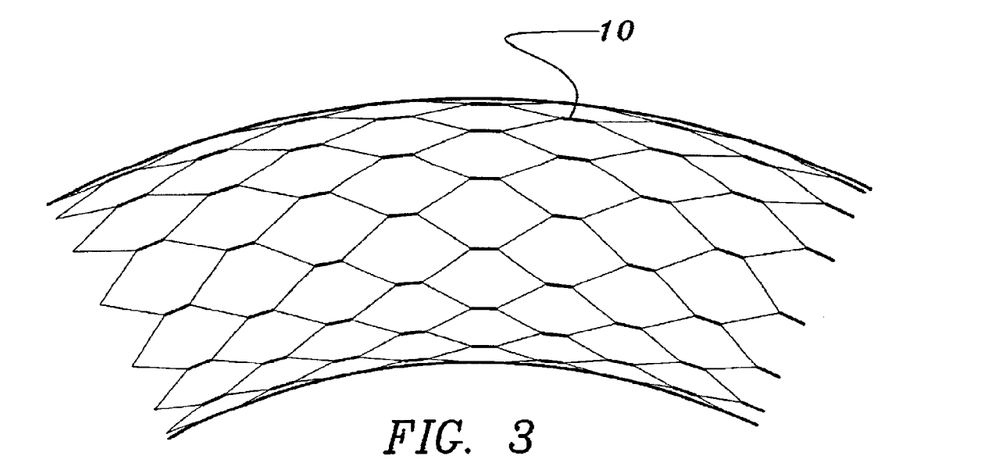
FIG. 3 shows an exterior design of a closed cell stent.
Figure 4:
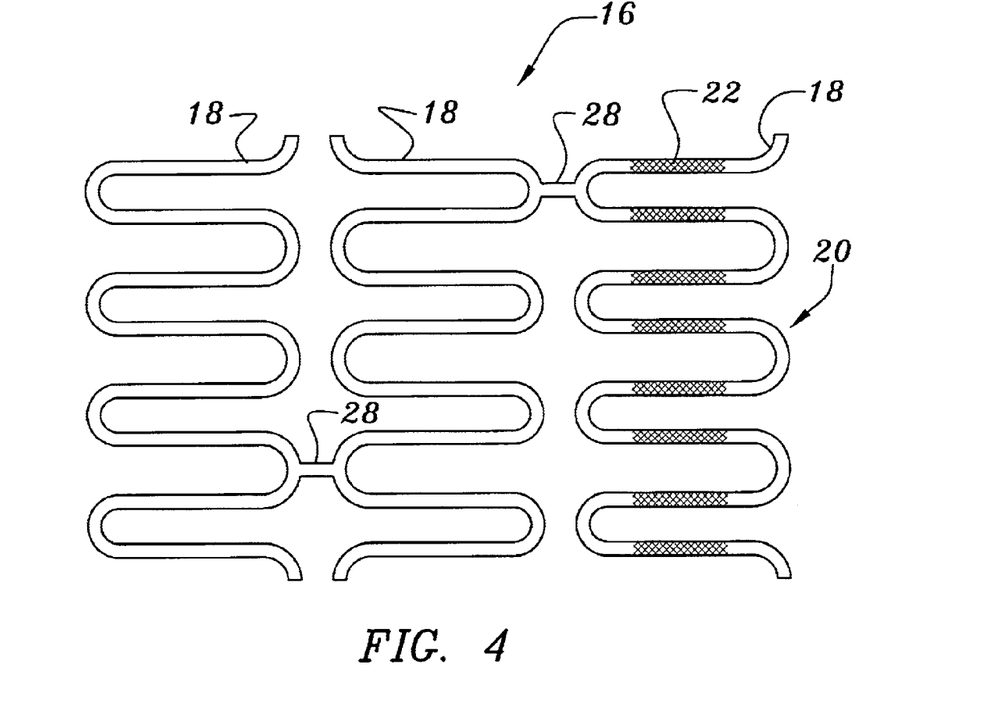
FIG. 4 shows a design of an open cell stent with a radiopaque coating on one section of the stent.

Referring to FIG. 1, the closed cell tubular stent design 10 has a longitudinal series of cells 12. As seen in FIG. 2, the cells 12 are interconnected by a bridge 14. The exterior look of such a stent 10 is seen in FIG. 3. In contrast, FIG. 4 shows the design of an open cell stent 16 having multiple open cells 18. One section 20 of the open cell stent 16 has a radiopaque coating 22.

Figure 5:
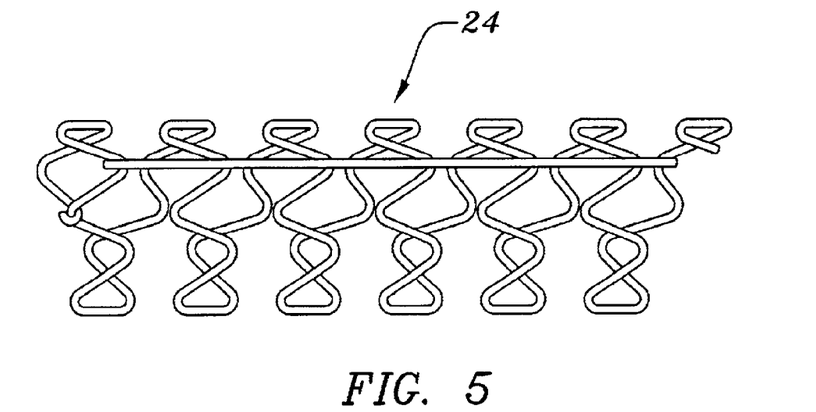
FIG. 5 shows a design of a coil stent.

A coil stent 24 design is shown in FIG. 5.

Figure 6:
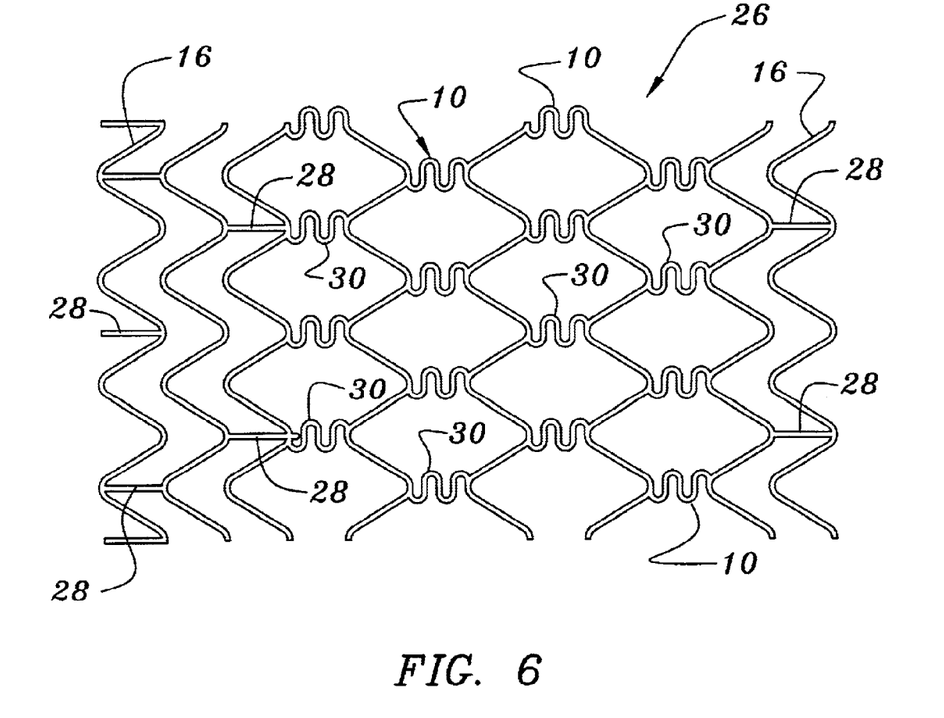
FIG. 6 shows a design of a structurally variable stent having an open cell design on the ends and a closed cell design at the center of the stent.

Referring to FIG. 6, the stent 26 of this invention is shown. The stent 26 has an open cell 16 configuration at each end and a closed cell design 10 at the center portion of the stent 26. Connecting struts 28 join the components.

Figure 7:
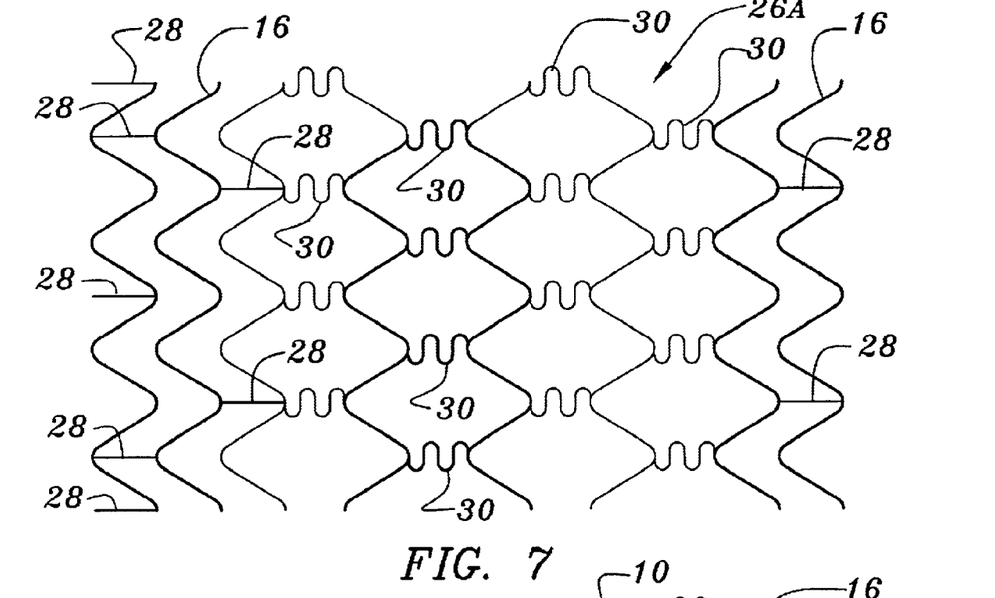
FIG. 7 shows a design of a structurally variable stent with variable thickness of the open and closed cell design.
Figure 8:
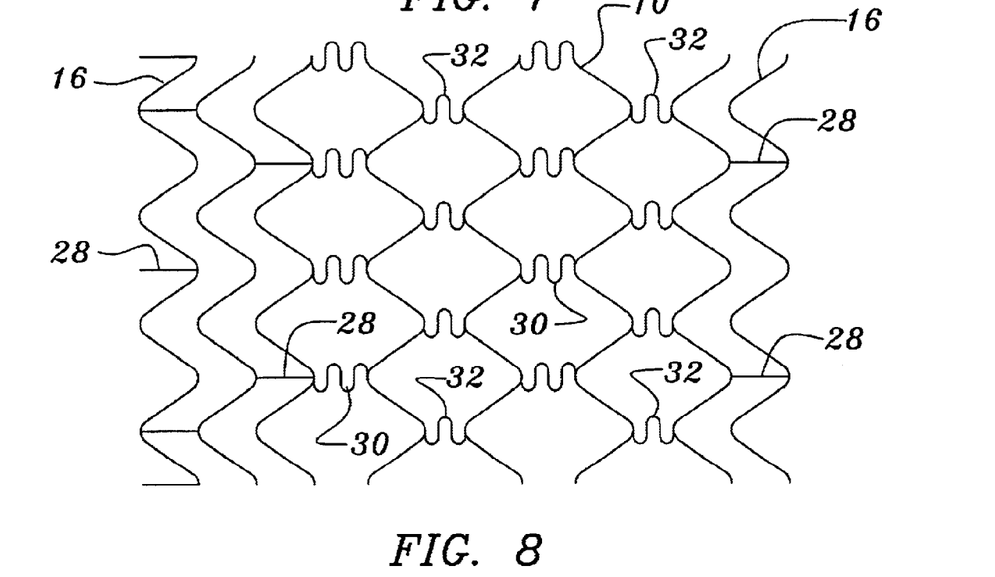
FIG. 8 shows a design of a structurally variable stent with open cell at the ends and closed cell at the mid-portion and alternating articulations between both the open and closed cell.

The stent 26A shown in FIG. 7 has the same configuration as stent 26 shown in FIG. 6, except that the thickness of the structure varies. The articulations 30 in a W-pattern are all the same. In FIG. 8, in contrast, articulations 32 are in the shape of an S-pattern while other articulations 30 remain in the W-pattern.

Figure 9:
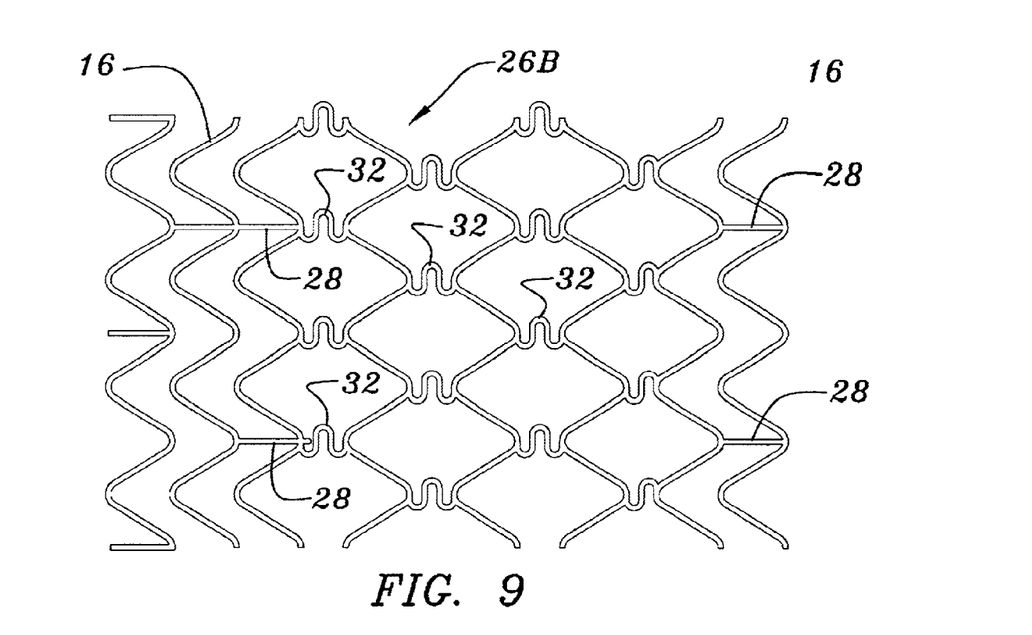
FIG. 9 shows a design of a structurally variable stent with both open and closed cell design and the articulations at the end of the closed cell design is an S-shape rather than a W-shape.
Figure 10:
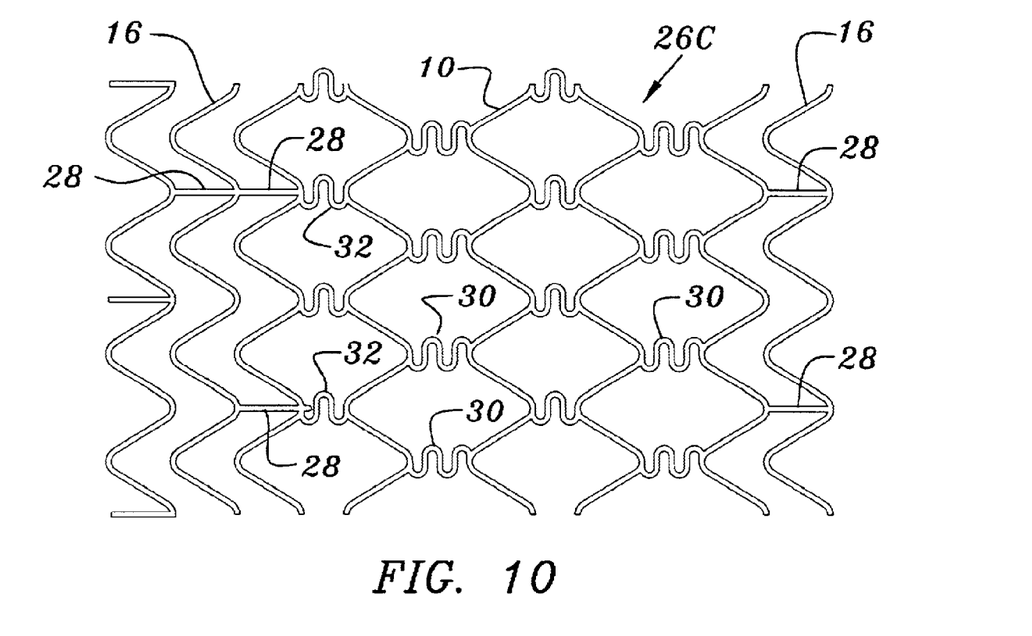
FIG. 10 shows a design of a structurally variable stent with both open and closed cell design and alternating articulations at various sections of the stent.

In FIG. 9, the stent 26B has a closed cell design 10 at its mid-portion and an open cell design 16 at each end. The articulations 32 are all in the shape of an S-pattern. In FIG. 10, the stent 26C has a closed cell design 10 at its mid-portion and an open cell design 16 at each end, but with alternating S-pattern 32 and W-pattern 30 articulations.

Figure 11:
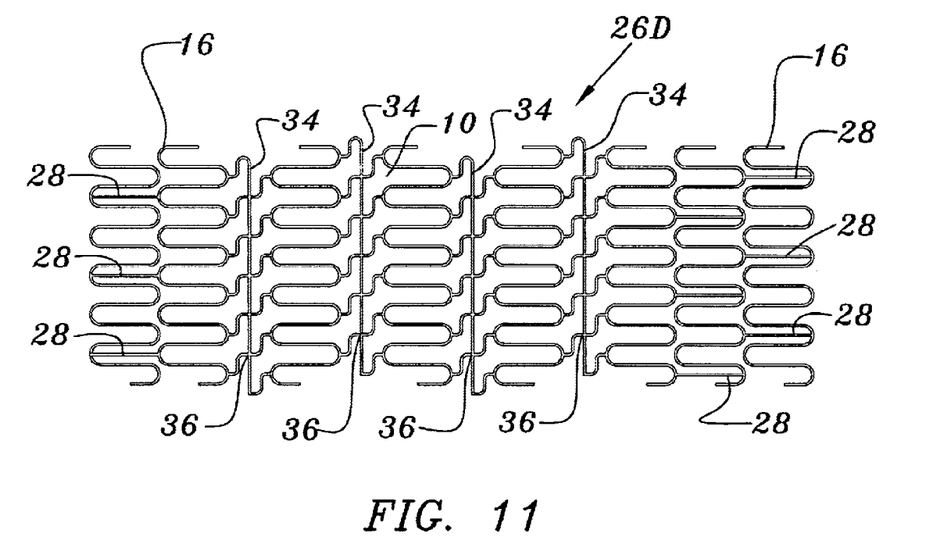
FIG. 11 shows a design of a structurally variable stent with an open cell design at the ends with multiple S-shapes and a straight articulating member and closed cell design and the mid-portion with a complex plus sign articulation.

In FIG. 11, the stent 26D has an open cell design 16 at its ends in an S-pattern, a straight articulating member 34, a closed cell 10 mid-portion with a complex plus sign pattern articulation 36.

Figure 12:
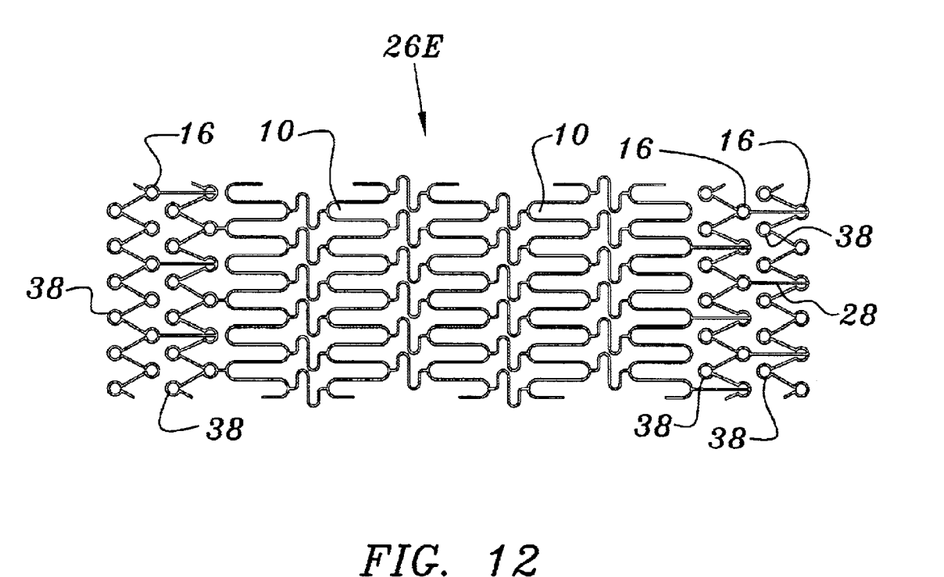
FIG. 12 shows a design of a structurally variable stent with a circle at a mid-portion of the open cell design.

In FIG. 12, the stent 26E has an open cell design 16 at its ends with a circle 38 in the open cell design. The center portion is a closed cell design 10.

Figure 13:
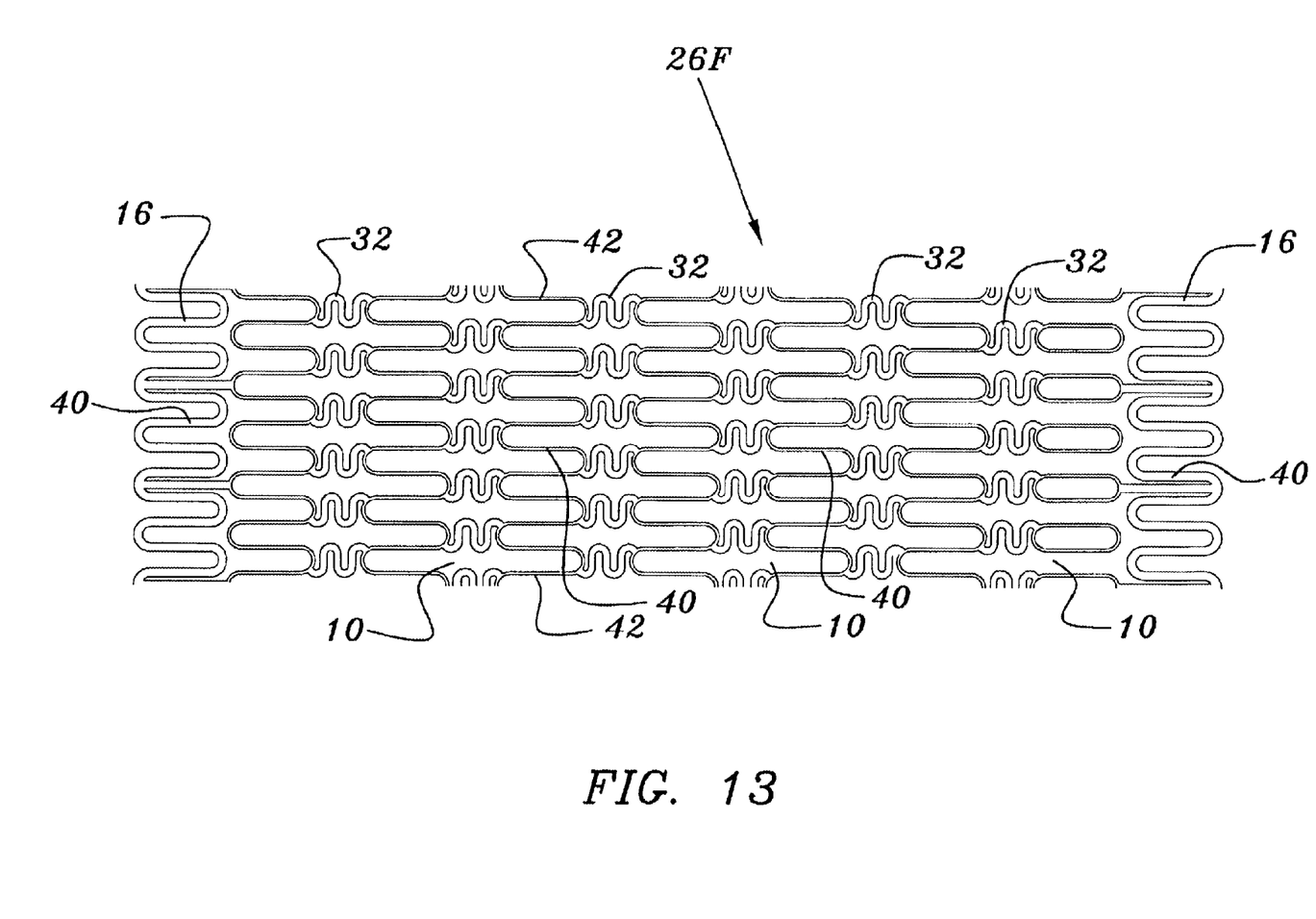
FIG. 13 shows a design of a structurally variable stent with different wall thickness along the length of the stent.

In FIG. 13, the stent 26F has thick 40 and thin 42 wall thickness.

The combination of an open cell 16 and closed cell 10 stent design creates a stent having both flexibility and radial strength along the length of the stent. The variable stent thickness 40 and 42 provides greater functional properties for coating the stent. If the coating is to enhance the radio opacity, then the ends can be made more radiopaque than the mid-portion. If the objective of a coating is to load more drugs then the ends of the stein can be thicker to allow for such coating. Since restenosis occurs in a stent invariably at its ends, a higher drug concentration at the ends can more thoroughly inhibit such restenosis.

The thickness of the open cell design 16 versus the closed cell design 10 may vary as seen in the drawings. The open cell design 16 is generally twenty-five percent thicker than the mid-portion or closed cell design 10.

Figure 14:
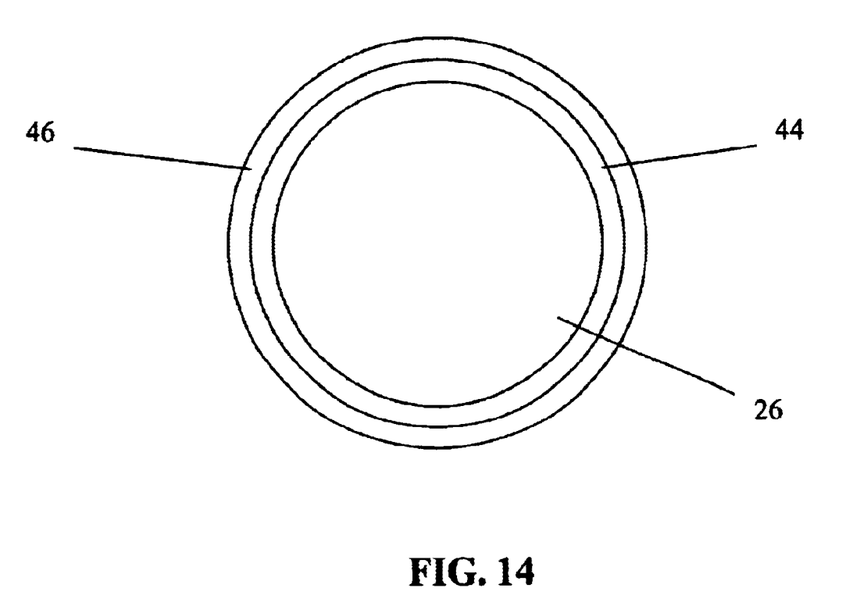
FIG. 14 shows a cross sectional view on a portion of the structurally variable stent including two coating layer.

Referring to FIG. 14 it is preferred to have two layers of coatings on the entire length of the stent 26. A base coat 44 of metal and a top coat 46 of metal enhances radio opacity of the stent 26. A base coat 44 of a polymeric coating has a top coat 46 of a drug which slowly diffuses out of the stent 26 over a period of time. The variable design stents 26–26F of this invention allows the loading of drugs at the ends to facilitate a graded release profile.

The stents 26–26F of this invention are longitudinal, cylindrical, metal structures having at least an open cell and closed cell design joined together by struts. The metal can be nickel-titanium alloy (NITINOL®) titanium, stainless steel or a noble base metal. A coating of at least two layers over the base metal has a depth not to exceed ten microns.

Typical coatings are set forth in U.S. Pat. Nos. 5,759,174; 5,725,572; 5,824,056; and 5,871,437 and are herein incorporated by reference.

The above description has described specific structural details embodying the variable stents of this invention. However, it will be within the skill of one having ordinary skill in the art to make modifications without departing from the spirit and scope of the underlying inventive concept of these structurally variable stents.

Having thus described the invention in detail the following is claimed:

1. A tubular stent comprising:
   a longitudinal cylindrical base structure having a first end portion, a second end portion, and a mid-portion interposed between the first and second end portions, the first and second end portions having a first pattern and the mid portion having a second pattern different from the first pattern, the second pattern including a plurality of articulations,
   a plurality of linear strut members connecting the mid portion to the first and second end portions, wherein the mid portion includes a plurality of articulations; and
   a surface coating having at least two layers coating the longitudinal cylindrical base structure, wherein the surface coating includes a drug inhibiting restenosis, with the drug having a higher concentration at the first and second end portions than at the mid portion.

2. The tubular stent of claim 1, wherein the plurality of articulations are a plurality of undulating members.

3. The tubular stent of claim 1, wherein the first pattern is an open coil design and the second pattern is a closed cell design.

4. The tubular stout of claim 1, wherein the longitudinal cylindrical base structure is made of a metal.

5. The tubular stunt of claim 1, wherein the longitudinal cylindrical base structure has a thickness greater at the first and second end portions than at the mid portion.

6. The tubular stent of claim 1, wherein the at least two layers comprise a material selected from the group consisting of metallic material, biological material, radiopaque material, synthetic material, polymeric material, and combinations thereof.

7. The tubular stent of claim 1, wherein the at least two layers have a thickness greater on the first and second end portions than on the mid portion.

8. The tubular stent of claim 1, wherein the at least two layers have a thickness of less than about 10 micron.

9. The tubular stent of claim 1, wherein the longitudinal cylindrical base structure has a thickness about twenty-five percent greater at the first and second end portions than at the mid portion.

* * * * *

UNITED STATES PATENT AND TRADEMARK OFFICE
CERTIFICATE OF CORRECTION

PATENT NO. : 6,908,480 B2
DATED : June 21, 2005
INVENTOR(S) : Swaminathan Jayaraman

It is certified that error appears in the above-identified patent and that said Letters Patent is hereby corrected as shown below:

Column 5,
Line 22, change "coil" to -- cell --.

Column 6,
Line 1, change "stout" to -- stent --.
Line 3, change "stunt" to -- stent --.

Signed and Sealed this

Thirteenth Day of December, 2005

JON W. DUDAS
*Director of the United States Patent and Trademark Office*